(12) United States Patent
Roth et al.

(10) Patent No.: US 7,523,637 B2
(45) Date of Patent: Apr. 28, 2009

(54) METHODS FOR CONTROLLING ONE OR MORE PARAMETERS OF A FLOW CYTOMETER TYPE MEASUREMENT SYSTEM

(75) Inventors: Wayne D. Roth, Leander, TX (US); Douglas E. Moore, Round Rock, TX (US)

(73) Assignee: Luminex Corporation, Austin, TX (US)

( * ) Notice: Subject to any disclaimer, the term of this patent is extended or adjusted under 35 U.S.C. 154(b) by 0 days.

(21) Appl. No.: 11/947,116

(22) Filed: Nov. 29, 2007

(65) Prior Publication Data

US 2008/0087068 A1    Apr. 17, 2008

Related U.S. Application Data

(62) Division of application No. 10/918,647, filed on Aug. 13, 2004, now Pat. No. 7,318,336.

(60) Provisional application No. 60/494,824, filed on Aug. 13, 2003.

(51) Int. Cl.
*G01N 21/00* (2006.01)

(52) U.S. Cl. ...................................... 73/1.02

(58) Field of Classification Search ............ 73/1.01, 73/1.02, 861.05, 861.07; 356/73; 436/8
See application file for complete search history.

(56) References Cited

U.S. PATENT DOCUMENTS

| | | | |
|---|---|---|---|
| 4,704,891 A | 11/1987 | Recktenwald et al. |
| 4,868,126 A | 9/1989 | Schwartz et al. |
| 5,084,394 A | 1/1992 | Vogt et al. |
| 5,380,663 A | 1/1995 | Schwartz et al. |
| 5,650,847 A | 7/1997 | Maltsev et al. |
| 5,736,330 A | 4/1998 | Fulton |
| 5,981,180 A | 11/1999 | Chandler et al. |
| 6,046,807 A | 4/2000 | Chandler |
| 6,057,107 A | 5/2000 | Fulton |
| 6,074,879 A | 6/2000 | Zelmanovic et al. |
| 6,139,800 A | 10/2000 | Chandler |
| 6,183,697 B1 | 2/2001 | Tanaka et al. |

(Continued)

FOREIGN PATENT DOCUMENTS

EP        0412431        10/1997

(Continued)

*Primary Examiner*—Hezron Williams
*Assistant Examiner*—John Fitzgerald
(74) *Attorney, Agent, or Firm*—Kevin L. Daffer; Mollie E. Lettang; Daffer McDaniel, LLP (57) ABSTRACT

Various methods for controlling one or more parameters of a flow cytometer type measurement system are provided. One embodiment includes monitoring parameter(s) of the measurement system during measurements of sample microspheres. The method also includes altering the parameter(s) in real time based on the monitoring. Another method includes monitoring a temperature proximate to the measurement system. One such method includes altering a bias voltage of an avalanche photo diode in response to the temperature using empirically derived data. A different such method includes altering output signals of a photomultiplier tube in response to the temperature using a characteristic curve. Some methods include monitoring a temperature of a fluid, in which sample microspheres are disposed, that will flow through the flow cytometer type measurement system. This method also includes determining a velocity of the sample microspheres in the measurement system from a viscosity of the fluid at the temperature.

7 Claims, 4 Drawing Sheets

U.S. PATENT DOCUMENTS

| | | |
|---|---|---|
| 6,200,101 B1 | 3/2001 | North, Jr. |
| 6,248,590 B1 | 6/2001 | Malachowski |
| 6,256,096 B1 | 7/2001 | Johnson |
| 6,268,222 B1 | 7/2001 | Chandler et al. |
| 6,350,619 B1 | 2/2002 | Mercolino et al. |
| 6,366,354 B1 | 4/2002 | Chandler |
| 6,372,506 B1 | 4/2002 | Norton |
| 6,411,904 B1 | 6/2002 | Chandler |
| 6,449,562 B1 | 9/2002 | Chandler et al. |
| 6,514,295 B1 | 2/2003 | Chandler et al. |
| 6,521,729 B1 | 2/2003 | Zelmanovic et al. |
| 6,524,793 B1 | 2/2003 | Chandler et al. |
| 6,528,165 B2 | 3/2003 | Chandler |
| 6,532,061 B2 | 3/2003 | Ortyn et al. |
| 6,549,275 B1 | 4/2003 | Cabuz et al. |
| 6,558,916 B2 | 5/2003 | Veerapandian et al. |
| 6,589,792 B1 | 7/2003 | Malachowski |
| 6,592,822 B1 | 7/2003 | Chandler |
| 6,618,140 B2 | 9/2003 | Frost et al. |
| 6,630,353 B1 | 10/2003 | Parce et al. |
| 6,654,119 B1 | 11/2003 | Gould et al. |
| 6,939,720 B2 | 9/2005 | Chandler et al. |
| 6,941,005 B2 | 9/2005 | Lary et al. |
| 7,012,689 B2 | 3/2006 | Sharpe |
| 7,227,625 B2 * | 6/2007 | Kobayashi et al. ............ 356/73 |
| 2003/0110826 A1 | 6/2003 | Shibata |
| 2003/0110840 A1 | 6/2003 | Arriaga et al. |
| 2003/0235919 A1 | 12/2003 | Chandler |
| 2005/0112541 A1 | 5/2005 | Durack et al. |
| 2005/0152593 A1 | 7/2005 | Calvin |
| 2005/0227362 A1 | 10/2005 | Lary et al. |
| 2006/0256338 A1 | 11/2006 | Gratton et al. |
| 2006/0259253 A1 | 11/2006 | Ellison et al. |

FOREIGN PATENT DOCUMENTS

| | | |
|---|---|---|
| EP | 1431745 | 6/2004 |

* cited by examiner

FIG. 7

METHODS FOR CONTROLLING ONE OR MORE PARAMETERS OF A FLOW CYTOMETER TYPE MEASUREMENT SYSTEM

PRIORITY CLAIM

This application is a divisional application from U.S. application Ser. No. 10/918,647 filed Aug. 13, 2004, now U.S. Pat. No. 7,318,336 which claims priority to U.S. Provisional Application No. 60/494,824 filed Aug. 13, 2003.

BACKGROUND OF THE INVENTION

1. Field of the Invention

This invention generally relates to methods for controlling one or more parameters of a flow cytometer type measurement system. Certain embodiments relate to methods that include altering one or more parameters of a flow cytometer type measurement system in real time based on monitoring of the parameter(s).

2. Description of the Related Art

The following descriptions and examples are not admitted to be prior art by virtue of their inclusion within this section.

Generally, flow cytometers provide measurements of fluorescence intensity of laser excited polystyrene beads or cells as they pass linearly through a flow chamber. However, flow cytometers can also be used to provide measurements of one or more properties of other particles. Some systems are configured to perform measurements of the level of light scattered by particles at 90° or 180° to the excitation source, two or more measurements of fluorescence used to determine classification, which is the particle "identity," and additional fluorescence measurements known as "reporters," typically used to quantify chemical reactions of interest. Each of the fluorescent measurements is made at different wavelengths.

As the measurement capability of flow cytometer type measurement instruments has improved, the applications in which flow cytometers can provide useful measurements has increased drastically. For example, flow cytometers have become increasingly useful in providing data for applications such as biological assays (e.g., displacement or competition assays, non-competition assays, enzyme assays), nucleic acid analysis, and combinatorial chemistry. In particular, the popularity of flow cytometer measurements has dramatically increased due to the speed with which assays can be performed particularly in comparison to other assay methods (e.g., conventional enzyme linked immunosorbent assay "ELISA" format).

Under normal circumstances, calibration of flow cytometers occurs as one or more preliminary steps in preparing instruments for proper use and measurement to ensure accurate and reliable assay results. In addition, unless the fluorescence channels of each flow cytometer are calibrated to read the same, there is no assurance as to the source of variation among samples. It is likely that one instrument will give different readings on the same sample on different days if robust and complete calibration methods are not employed. Similarly, if there is no assurance that any two instruments will provide the same results even if properly set up, although flow cytometry may provide a better measure of identifying and distinguishing between cells in a sample, its use as a clinical instrument may be diminished.

Accordingly, many different methods for calibrating a flow cytometer have been developed. Initially, significant work was done to develop calibration methods that reduced the level of involvement of the operator in calibration to increase the accuracy of the calibration. This work led, in large part, to the automation of many steps of the calibration of flow cytometers. In addition, significant work was done to improve the accuracy of the calibration in other ways. For example, this work has led to advancement in calibrations such as using calibration standards that have uniform and constant properties. In particular, since the properties of biological samples can change over time, biological calibration standards for flow cytometers have generally been replaced with synthetic calibration standards (e.g., polymeric microspheres or particles) that have more stable properties. In addition, typically the calibration microspheres have properties (e.g., size, volume, surface characteristics, granularity properties, refractive index, fluorescence, etc.) that are substantially similar (i.e., as close as possible) to the properties of the test microspheres. Such calibration microspheres were believed to increase the accuracy of the flow cytometer by performing calibration at values that are as close as possible to the values that were expected during testing.

Attempts to improve the calibration of flow cytometers have also led to increasing the number of parameters of the flow cytometer that are accounted for by calibration. For example, the laser excitation, detectors, and electronics of flow cytometer measurement systems vary over time, which affects the final measurement. Therefore, these, and sometimes other, parameters of flow cytometers are typically accounted for by calibration methods.

Other parameters, which are more difficult to control, also affect the measurements of a flow cytometer. One such parameter is sample velocity. One example of a method for measuring sample velocity is illustrated in U.S. Pat. No. 6,532,061 Ortyn et al., which is incorporated by reference as if fully set forth herein. In this method, objects are entrained in a flow of fluid, which is caused to flow through the sensitive or measurement volume. In each of these embodiments, optical gratings having a substantially uniform pitch are employed to modulate light received from the moving objects. The modulated light is converted into an electrical signal, which is digitized and then processed using a Fast Fourier Transform (FFT) to determine the velocity of the object. There are, however, several disadvantages to the methods and systems described by Ortyn et al. for measuring sample velocity. For example, the methods require fairly complex optical gratings and software. In addition, due to the precision required for the optical gratings and the complexity of manufacturing, the optical gratings may be fairly expensive. Furthermore, the sample velocity measurements may be somewhat inaccurate due, for example, to the optical distortion of the detected light by the moving objects.

However, the most significant error contribution in flow cytometer measurements is generally caused by temperature variance. In addition, it has been found that the effect of temperature variance on the measurements performed by a flow cytometer is not adequately accounted for by the presently available calibration methods. For example, the methods and systems described by Ortyn et al., although attempting to correct for a number of parameters, do not take into account temperature variations and how they affect the measurements of a flow cytometer. Therefore, although many different calibration methods are available, additional improvements to each of these methods can be made by more accurately accounting for temperature variations during different flow cytometer measurements or during individual flow cytometer measurements.

Accordingly, it may be advantageous to develop methods for controlling at least the major error contributing components of flow cytometer measurement systems, which could be combined to produce a real time calibration scheme.

SUMMARY OF THE INVENTION

As set forth in detail above, the most significant error contribution in flow cytometers is generally caused by temperature variance. Since the temperature may be a measured quantity, and the physics behind its effects are known, it is possible to reduce, and even nullify, the most critical of these error sources.

Several measurement error contributors and real time correction techniques for the measurement error contributors have been identified. In addition, a real time fine-tuning method using calibration microspheres uniquely identifiable via a diameter at least slightly different from those being measured, which may be included in microsphere sample mixes, has been created. Added features of the fine-tuning process may include real time identification of system health, correction of non-linearities in one or more channels, and/or the significant extension of a flow cytometer measurement system's useful reporter dynamic range. The described embodiments are useful to compensate for system variations primarily due to temperature, thus extending the calibrated range of operation.

In addition, it is to be noted that several different embodiments of methods for controlling one or more parameters of a flow cytometer type measurement system are described herein. It is to be understood that each of the methods may be used and performed separately. In addition, two or more of the methods may be used or performed in combination depending on, for example, the variability in various components of the measurement system and/or the desired accuracy of the measurement system.

One embodiment of the present invention relates to a method for controlling one or more parameters of a flow cytometer type measurement system. The method includes monitoring the one or more parameters of the flow cytometer type measurement system during measurements of sample microspheres by the measurement system. The method also includes altering the one or more parameters in real time based on the monitoring.

In one embodiment, monitoring the one or more parameters may include monitoring the one or more parameters using measurements of calibration microspheres. The calibration microspheres have diameters that are different than (e.g., less than) diameters of the sample microspheres. In some embodiments, the one or more parameters may include output signals produced by detectors of the measurement system. The output signals are responsive to light scattered by the sample microspheres.

In another embodiment, monitoring the one or more parameters may include monitoring the one or more parameters using measurements of calibration microspheres. In this embodiment, the calibration microspheres have diameters that are different than (e.g., less than) diameters of the sample microspheres, and at least some of the calibration microspheres have different spectral addresses. In one such embodiment, the one or more parameters may include a dynamic range of the measurement system. In another embodiment, altering the parameter(s) may include extending a linear dynamic range of one or more channels of the measurement system. In an additional embodiment, the one or more parameters may include a measurement of system health. The measurement of system health may include health of a classification channel, health of a reporter channel, or a combination thereof. In some embodiments, the one or more parameters may include linearity in the measurements of the sample microspheres. In such an embodiment, the measurements may include measurements of a classification channel, measurements of a reporter channel, or a combination thereof. In another such embodiment, altering the parameter(s) may include substantially correcting any non-linearity in the measurements.

In some embodiments, the parameter(s) may include a parameter of an avalanche photo diode of the measurement system. In one such embodiment, the method may also include determining a correction factor to be used in altering the parameter(s) using empirically derived data. In another embodiment, the parameter(s) may include a parameter of a photomultiplier tube of the measurement system.

In a further embodiment, the parameter(s) may include a velocity of the sample microspheres. In one such embodiment, monitoring the parameter(s) may include monitoring a temperature of a fluid in which the sample microspheres are disposed and determining the velocity of the sample microspheres from the temperature. In some embodiments, the method may also include calibrating the one or more parameters prior to the measurements of the sample microspheres. Each of the embodiments of the method described above may include any other step(s) described herein.

Another embodiment relates to a different method for controlling one or more parameters of a flow cytometer type measurement system. This method includes monitoring a temperature proximate to the flow cytometer type measurement system. The method also includes altering a bias voltage of an avalanche photo diode of the measurement system in response to the temperature using empirically derived data to substantially correct for variation in a gain of the avalanche photo diode due to the temperature.

In one embodiment, the method may also include generating the empirically derived data by applying a substantially constant light level to the avalanche photo diode at one or more temperatures and recording a current output of the avalanche photo diode for multiple bias voltages at the one or more temperatures. In another embodiment, altering the parameter(s) is performed before sample measurements are performed by the measurement system. In such an embodiment, the bias voltage may be substantially constant throughout the sample measurements. In a different embodiment, monitoring the parameter(s) and altering the parameter(s) are performed in real time.

In some embodiments, the method may also include varying the bias voltage of the avalanche photo diode while calibration microspheres that emit light of known intensity are measured by the measurement system until a predetermined signal level is obtained from the avalanche photo diode. In one such embodiment, the method may further include determining a corresponding relative current for the avalanche photo diode from a reverse bias voltage for the avalanche photo diode, the bias voltage at the predetermined signal level, and the temperature. This embodiment of the method may also include determining the bias voltage using the corresponding relative current, the temperature, the reverse bias voltage, and the empirically derived data. Each of the embodiments of the method described above may include any other step(s) described herein.

An additional embodiment relates to yet another method for controlling one or more parameters of a flow cytometer type measurement system. This method includes monitoring a temperature proximate to the flow cytometer type measurement system. The method also includes altering an output signal of a photomultiplier tube of the measurement system in response to the temperature using a characteristic curve for the photomultiplier tube to substantially correct for variation in a gain of the output signal of the photomultiplier tube. The gain of the photomultiplier tube varies approximately linearly in response to the temperature. In some embodiments, the photomultiplier tube is part of a reporter channel of the measurement system. In another embodiment, the characteristic curve for the photomultiplier tube varies with detection wavelength and cathode construction of the photomultiplier tube. Each of the embodiments of the method described above may include any other step(s) described herein.

Another embodiment relates to yet a different embodiment of a method for controlling one or more parameters of a flow cytometer type measurement system. This method includes setting a voltage of a photomultiplier tube of the measurement system at a first value and a second value. The method also includes measuring an output current of the photomultiplier tube at the first and second values. In addition, the method includes determining a calibration voltage of the photomultiplier tube from a log of the first and second values versus a log of the output currents at the first and second values. The method further includes applying the calibration voltage to the photomultiplier tube. The method also includes testing the photomultiplier tube to determine if one or more parameters of the photomultiplier tube are within predetermined tolerances. Each of the embodiments of the method described above may include any other step(s) described herein.

An additional embodiment relates to another method for controlling one or more parameters of a flow cytometer type measurement system. This method includes determining a calibration voltage of a detector of the measurement system using successive approximation. The method also includes applying the calibration voltage to the detector. In one embodiment, the detector may include an avalanche photodiode. In a different embodiment, the detector may include a photomultiplier tube.

In one embodiment, the method may include comparing the calibration voltage to a breakdown voltage of the detector and repeating the determination of the calibration voltage if the calibration voltage exceeds the breakdown voltage. A different embodiment of the method includes collecting and processing detector samples to determine a detector signal level. In one such embodiment, the method may include comparing the detector signal level to a calibration target signal level and if the detector signal level is above the calibration target signal level, then reducing a bias voltage of the detector, and repeating the determination of the calibration voltage. In another such embodiment, the method may include comparing the detector signal level to a calibration target signal level and if the detector signal level is not within a predetermined range of the calibration target signal level, then repeating determination of the calibration voltage until all desired detector voltage levels have been attempted. Each of the embodiments of the method described above may also include any other step(s) described herein.

A further embodiment relates to a different method for controlling one or more parameters of a flow cytometer type measurement system. This method includes monitoring a temperature of a fluid that will flow through the flow cytometer type measurement system. Sample microspheres are disposed in the fluid. The method also includes determining a velocity of the sample microspheres in the measurement system from a viscosity of the fluid at the temperature.

In one embodiment, the method may also include determining a length of time that one of the sample microspheres will be present in a detection window of the measurement system based on the velocity. In some embodiments, the method may include determining a length of time in which one of the sample microspheres will travel from one detection window of the measurement system to another detection window of the measurement system based on the velocity. In another embodiment, the method may include determining when one of the sample microspheres will be present in a detection window of the measurement system based on the velocity. In yet another embodiment, the method may include controlling a sampling interval for one or more detection windows of the measurement system to compensate for the velocity.

In an additional embodiment, monitoring the parameter(s) and determining the velocity are performed prior to performing measurements of the sample microspheres with the measurement system. In some embodiments, the method may include determining one or more properties of output signals of the measurement system from the velocity. In one such embodiment, the method includes correcting the output signals for error due to the velocity using correction factors. The correction factors are determined using empirical measurements. In another embodiment, the measurement system is configured to maintain a substantially constant pressure of the fluid during measurements of the sample microspheres.

In one embodiment, determining the velocity may include determining the velocity from a table, from Poiseuille's equation, or from predetermined values of velocity versus temperature. In some such embodiments, the method may also include controlling a pressure of the fluid during measurements of the sample microspheres based on the velocity. Each of the embodiments of the method described above may include any other step(s) described herein.

A different embodiment relates to another method for controlling one or more parameters of a flow cytometer type measurement system. This method includes measuring a time in which a microsphere travels from a first detection window of the flow cytometer type measurement system to a second detection window of the measurement system. The method also includes altering an applied pressure of the measurement system such that the time is substantially constant. In one embodiment, the time is an average time. The microsphere may be a sample microsphere or a calibration microsphere. Measuring the time may include measuring light scattered by the microsphere in the first and second detection windows. In another embodiment, measuring the time may include measuring light scattered by the microsphere in the first and second detection windows with one detector. The light scattered by the microsphere in the first and second detection windows may be directed to the one detector by one beamsplitter. The method may or may not be performed in real time. Each of the embodiments of the method described above may include any other step(s) described herein.

A further embodiment relates to a different method for controlling one or more parameters of a flow cytometer type measurement system. This method includes measuring an average time in which microspheres travel from a first detection window of the flow cytometer type measurement system to a second detection window of the measurement system. The microspheres may include sample microspheres, calibration microspheres, or calibration and sample microspheres. The method also includes comparing the average time to a reference time in which a reference microsphere traveled from the first detection window to the second detection window. In addition, the method includes altering an applied pressure of the measurement system if a difference between the average time and the reference time is larger than a predetermined value.

In one embodiment, altering the applied pressure includes increasing the applied pressure if the average time is larger than the reference time. Alternatively, altering the applied pressure includes decreasing the applied pressure if the average time is smaller than the reference time. In some embodiments, the predetermined value is selected to compensate for known time variation mechanisms of the measurement system. This method may or may not be performed in real time. Each of the embodiments of the method described above may include any other step(s) described herein.

BRIEF DESCRIPTION OF THE DRAWINGS

Other objects and advantages of the invention will become apparent upon reading the following detailed description and upon reference to the accompanying drawings in which.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

Several different embodiments of methods for controlling one or more parameters of a flow cytometer type measurement system are described herein. As noted above, each of the methods may be used and performed separately. In addition, two or more of the methods may be used or performed in combination depending on, for example, the variability in various components of the measurement system and/or the desired accuracy of the measurement system.

Although embodiments are described herein with respect to microspheres or polystyrene beads, it is to be understood that the measurement systems and methods may also be used with microparticles, gold nanoparticles, beads, microbeads, latex particles, latex beads, fluorescent beads, fluorescent particles, colored particles, colored beads, and cells. The microspheres may serve as vehicles for molecular reactions. Examples of appropriate microspheres, beads, and particles are illustrated in U.S. Pat. No. 5,736,330 to Fulton, U.S. Pat. No. 5,981,180 to Chandler et al., U.S. Pat. No. 6,057,107 to Fulton, U.S. Pat. No. 6,268,222 to Chandler et al., U.S. Pat. No. 6,449,562 to Chandler et al., U.S. Pat. No. 6,514,295 to Chandler et al., U.S. Pat. No. 6,524,793 to Chandler et al., and U.S. Pat. No. 6,528,165 to Chandler, which are incorporated by reference as if fully set forth herein. The measurement systems and methods described herein may be used with any of the microspheres, beads, and particles described in these patents. In addition, microspheres for use in flow cytometry may be obtained from manufacturers such as Luminex Corp., Austin, Tex. The terms "beads" and "microspheres" are used interchangeably herein.

Figure 1:
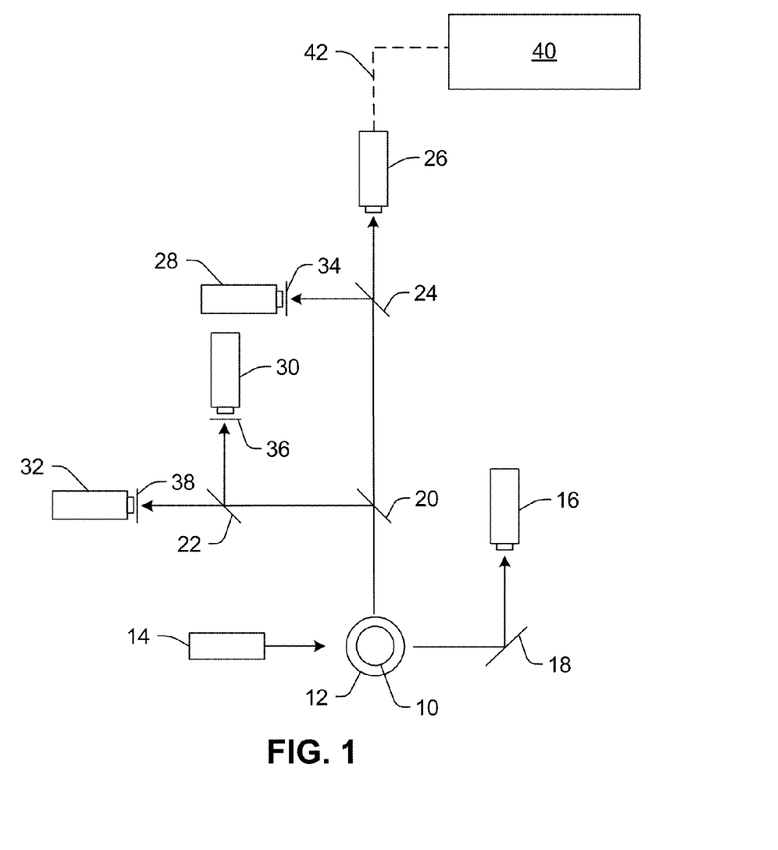
FIG. 1 is a schematic diagram illustrating one example of a measurement system that may be used to carry out the methods described herein.

FIG. 1 illustrates one example of a measurement system that may be used to perform the methods described herein. In particular, one or more parameters of the measurement system illustrated in FIG. 1 may be determined, monitored, altered, and/or controlled according to the methods described herein. It is noted that the figures described herein are not drawn to scale. In particular, the scale of some of the elements of the figures are greatly exaggerated to emphasize characteristics of the elements. Some elements of the measurement systems have not been included in the figures for the sake of clarity.

In FIG. 1, the measurement system is shown along a plane through the cross-section of cuvette 12 through which microspheres 10 flow. In one example, the cuvette may be a standard quartz cuvette such as that used in standard flow cytometers. Any other suitable type of viewing or delivery chamber, however, may also be used to deliver the sample for analysis. The measurement system includes light source 14. Light source 14 may include any appropriate light source known in the art such as a laser. The light source may be configured to emit light having one or more wavelengths such as blue light or green light. Light source 14 may be configured to illuminate the microspheres as they flow through the cuvette. The illumination may cause the microspheres to emit fluorescent light having one or more wavelengths or wavelength bands. In some embodiments, the system may include one or more lenses (not shown) configured to focus light from the light source onto the microspheres or the flowpath. The system may also include more than one light source. In one embodiment, the light sources may be configured to illuminate the microspheres with light having different wavelengths or wavelength bands (e.g., blue light and green light). In some embodiments, the light sources may be configured to illuminate the microspheres at different directions.

Light scattered forwardly from the microspheres may be directed to detection system 16 by folding mirror 18 or another suitable light directing component. Alternatively, detection system 16 may be placed directly in the path of the forwardly scattered light. In this manner, the folding mirror or other light directing components may not be included in the system. In one embodiment, the forwardly scattered light may be light scattered by the microspheres at an angle of about 180° from the direction of illumination by light source 14, as shown in FIG. 1. The angle of the forwardly scattered light may not be exactly 180° from the direction of illumination such that incident light from the light source may not impinge upon the photosensitive surface of the detection system. For example, the forwardly scattered light may be light scattered by the microspheres at angles less than or greater than 180° from the direction of illumination (e.g., light scattered at an angle of about 170°, about 175°, about 185°, or about 190°).

Light scattered by the microspheres at an angle of about 90° from the direction of illumination may also be collected. In one embodiment, this scattered light may be separated into more than one beam of light by one or more beamsplitters or dichroic mirrors. For example, light scattered at an angle of about 90° to the direction of illumination may be separated into two different beams of light by beamsplitter 20. The two different beams of light may be separated again by beamsplitters 22 and 24 to produce four different beams of light. Each of the beams of light may be directed to a different detection system, which may include one or more detectors. For example, one of the four beams of light may be directed to detection system 26. Detection system 26 may be configured to detect light scattered by the microspheres.

Scattered light detected by detection system 16 and/or detection system 26 may generally be proportional to the volume of the particles that are illuminated by the light source. Therefore, output signals of detection system 16 and/or output signals of detection system 26 may be used to determine a diameter of the particles that are in the illumination zone or detection window. In addition, the output signals of detection system 16 and/or detection system 26 may be used to identify more than one particle that are stuck together or that are passing through the illumination zone at approximately the same time. Therefore, such particles may be distinguished from other sample microspheres and calibration microspheres. Furthermore, the output signals of detection system 16 and/or detection system 26 may be used to distinguish between sample microspheres and calibration microspheres as described herein based on size.

The other three beams of light may be directed to detection systems 28, 30, and 32. Detection systems 28, 30, and 32 may be configured to detect fluorescence emitted by the microspheres. Each of the detection systems may be configured to detect fluorescence of a different wavelength or a different range of wavelengths. For example, one of the detection systems may be configured to detect green fluorescence. Another of the detection systems may be configured to detect yellow-orange fluorescence, and the other detection system may be configured to detect red fluorescence.

In some embodiments, spectral filters 34, 36, and 38 may be coupled to detection systems 28, 30, and 32, respectively. The spectral filters may be configured to block fluorescence of wavelengths other than that which the detection systems are configured to detect. In addition, one or more lenses (not shown) may be optically coupled to each of the detection systems. The lenses may be configured to focus the scattered light or emitted fluorescence onto a photosensitive surface of the detectors.

The detector's output current is proportional to the fluorescent light impinging on it and results in a current pulse. The current pulse may be converted to a voltage pulse, low pass filtered, and then digitized by an A/D converter. Processor 40 such as a DSP integrates the area under the pulse to provide a number which represents the magnitude of the fluorescence. In addition, the processor may perform additional functions described herein (e.g., monitoring one or more parameters of the flow cytometer type measurement system, altering the one or more parameters in real time based on the monitored parameter(s), etc.). As shown in FIG. 1, processor 40 may be coupled to detector 26 via transmission medium 42. Processor 40 may also be coupled to detector 26 indirectly via transmission medium 42 and one or more other components (not shown) such as the A/D converter. The processor may be coupled to other detectors of the system in a similar manner.

In some embodiments, the output signals generated from fluorescence emitted by the microspheres may be used to determine an identity of the microspheres and information about a reaction taking place on the surface of the microspheres. For example, output signals of two of the detection systems may be used to determine an identity of the microspheres, and output signals of the other detection system may be used to determine a reaction taking place on the surface of the microspheres. Therefore, the selection of the detectors and the spectral filters may vary depending on the type of dyes incorporated into or bound to the microspheres and/or the reaction being measured (i.e., the dye(s) incorporated into or bound to the reactants involved in the reaction).

The detection systems that are used to determine an identity of the sample microspheres (e.g., detection systems 28 and 30) may be APDs, a PMT, or another photodetector. The APDs may be corrected in real time for gain variation as a function of temperature as described herein. The detection system that is used to identify a reaction taking place of the surface of the microspheres (e.g., detection system 32) may be a PMT, an APD, or another form of photodetector. The PMT may be corrected using a simple multiplier derived from PMT characteristic curves that can be applied to the output signals of the PMT as described herein. The detectors and the measurement system may be further configured as described herein.

Although the system of FIG. 1 is shown to include two detection systems having two different detection windows for distinguishing between microspheres having different dye characteristics, it is to be understood that the system may include more than two such detection windows (i.e., 3 detection windows, 4 detection windows, etc.). In such embodiments, the system may include additional beamsplitters and additional detection systems having other detection windows. In addition, spectral filters and/or lenses may be coupled to each of the additional detection systems.

In another embodiment, the system may include two or more detection systems configured to distinguish between different materials that are reacted on the surface of the microspheres. The different reactant materials may have dye characteristics that are different than the dye characteristics of the microspheres.

Additional examples of measurement systems that may be used to perform the methods described herein are illustrated in U.S. Pat. No. 5,981,180 to Chandler et al., U.S. Pat. No. 6,046,807 to Chandler, U.S. Pat. No. 6,139,800 to Chandler, U.S. Pat. No. 6,366,354 to Chandler, U.S. Pat. No. 6,411,904 to Chandler, U.S. Pat. No. 6,449,562 to Chandler et al., and U.S. Pat. No. 6,524,793 to Chandler et al., which are incorporated by reference as if fully set forth herein. The measurement system described herein may also be further configured as described in these patents.

In flow cytometer type measurement systems, scattered light and bead identity detection are generally performed using avalanche photo diodes (APDs) as the light sensors. APDs are advantageous over other detectors since the output current level or "gain" of an APD may be varied over a wide range through application of a reverse bias voltage. The gain, which may be expressed in terms of the electrons that flow as a result of a constant number of input photons, is proportional to the magnitude of the applied bias voltage. Unfortunately, the conversion from input photons to output electrons is highly temperature dependent. Therefore, an APD is highly temperature dependent and much more so than any other element in flow cytometer type measurement systems.

Accordingly, one embodiment of a method for controlling one or more parameters of a flow cytometer type measurement system includes monitoring a temperature proximate to the flow cytometer type measurement system. The method also includes altering a bias voltage of an APD of the measurement system in response to the temperature.

Each APD is rated by the manufacturer in terms of the reverse bias voltage (V60) that will achieve an output current 60 times greater than that of a silicon diode under substantially identical illumination. Depending on the individual device, V60 can range from tens of volts to more than 100 volts.

Since an APD's output is nonlinear with respect to temperature, a constant compensation factor cannot be used across the entire operating range of the APD. Empirical measurements of current output vs. temperature can be utilized in developing a comprehensive compensation method. In other words, a correction factor to be used in altering parameter(s) of the APD may be determined using empirically derived data. In particular, the bias voltage of the APD can be altered using empirically derived data to substantially correct for variation in a gain of the avalanche photodiode due to the temperature.

Figure 2:
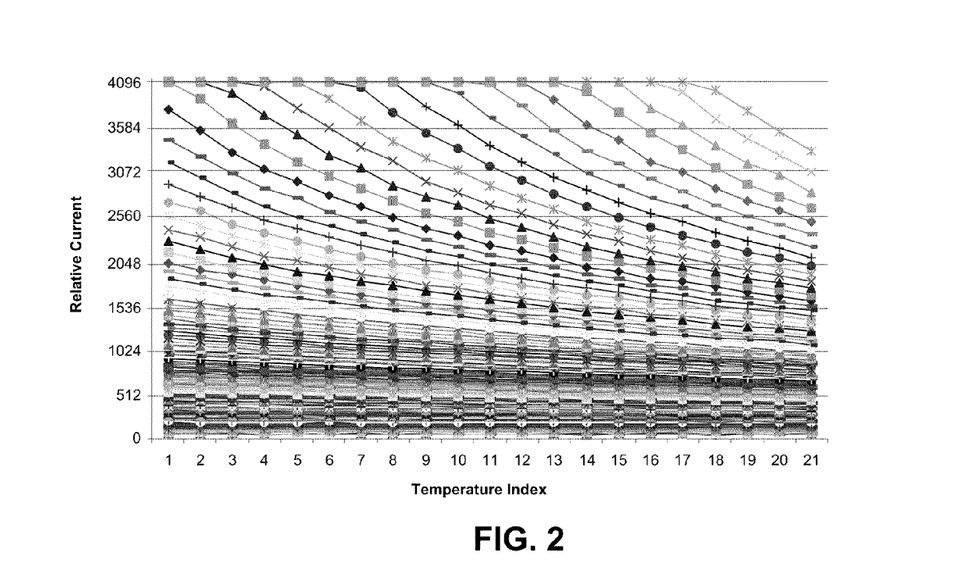
FIG. 2 is a graph illustrating one example of multiple bias curves showing the response of an APD, having a reverse bias voltage (V60) of 130 volts, as a function of temperature.

To characterize the APD's response with empirically derived data, a substantially constant light level is applied to the APD at one or more temperatures. At one or more given temperatures, the current output of the APD is recorded for multiple bias voltages. The temperature is changed (e.g., in whole degree increments), and current measurements are again repeated at multiple bias voltages. The resultant data collection (such as that shown in FIG. 2) fully describes the illumination vs. current profile of that particular V60 device over temperature. To capture the response of a plurality of different devices, these measurements may be repeated for APDs with different V60 ratings.

In one embodiment, the bias curve tables may be utilized to correct for temperature in the following manner. During initial system calibration, calibration microspheres that emit light of known intensity are introduced to the system. The calibration microspheres flow through the system, and while the calibration microspheres are measured by the measurement system, the bias voltage is varied until a predetermined signal level is obtained from the APD. The V60 for the detector, the bias voltage at the predetermined signal level, and temperature are then used as an index into the APD response tables in order to insert the APD's current reading into the table (the R value).

In another embodiment, the bias curve tables may be generated in the following manner. A source of constant light output, such as a light emitting diode (LED), could be used to illuminate the photosensitive area of the APD remotely via a fiber optic cable. The APD could then be placed in an environmental chamber that has the capability to change the ambient temperature to which the APD is exposed. A measurement system would then record the current output of the APD (R value) while both the temperature, and the bias voltage to the APD, are varied.

During a normal sample run, a temperature proximate to the flow cytometer type measurement system may be monitored. The bias voltage may then be determined using the desired relative current, the temperature, and the empirically derived data. For example, the R value, measured temperature, and V60 parameters can be used as inputs to the APD response table to find the corresponding bias voltage. If the measured temperature lies between table entries, the readings corresponding to the closest temperature entries can be interpolated to find the best bias voltage. The bias voltage obtained from the table is applied to the APD to correct for its gain variation with temperature. Since the sample run is typically less than two minutes in duration, and the temperature varies little over this amount of time, it is generally sufficient to make a single bias correction at the beginning of a sample run and hold this bias for the duration of the run. In other words, the bias voltage may be altered before sample measurements are performed by the measurement system, and the bias voltage may be substantially constant through the sample measurements. However, it is possible that the temperature proximate the measurement system is monitored over time during the sample run, and the bias voltage of the APD may be altered accordingly. In this manner, monitoring the temperature and altering the bias voltage of the APD may be performed in real time.

The reporter channel of some flow cytometer measurement systems includes a photo-multiplier tube (PMT) as the photosensitive detector. The reporter channel may be generally defined as the channel that is used to identify a material involved in a reaction taking place on the surface of the microspheres or a material bound to the surface of the microspheres. PMTs generate electrical current in proportion to the quantity of light illuminating the photocathode, the applied bias voltage, and the number of internal dynodes in the PMT. In a flow cytometer, the PMT's bias voltage is typically used as a "control" point to normalize the current output for a given level of fluorescent light. The method used currently to find the normalized voltage during a calibration procedure is empirical in that a measurement is taken, and an educated guess is made as to a PMT bias setting that is likely to result in an output closer to the desired value. Often, many iterations are required before the output error level is within an acceptable range. It would, therefore, be advantageous to shorten the calibration time, and thus reduce the quantity of calibration reagents used to find the best PMT voltage. Several different methods are described below that will accelerate the calibration process beyond what is currently available.

Figure 3:
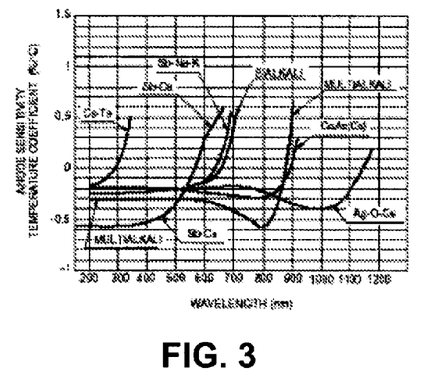
FIG. 3 is a graph illustrating the response of various PMTs as a function of temperature.

Due to a substantially linear response to temperature, PMTs are much simpler to compensate for temperature variations than APDs. For example, one embodiment of a method for controlling one or more parameters of a flow cytometer type measurement system includes monitoring a temperature proximate to the flow cytometer type measurement system. The temperature is typically measured as close as possible to the PMT, although the precise location is not critical due to the PMT's relatively mild temperature variation rate. The method also includes altering an output signal of a PMT of the measurement system in response to the temperature using a characteristic curve for the PMT to substantially correct for variation in a gain of the output signal of the PMT due to temperature. The gain of the PMT will vary approximately linearly in response to the temperature. In addition, the characteristic curve for the PMT will vary with detection wavelength and cathode construction. In this manner, for a given detection wavelength and cathode construction, the response of a PMT with respect to temperature can be expressed via a simple linear relationship, as shown in FIG. 3, which is taken from "Photomultiplier tube—Principal to Application," Hamamatsu Photonics K.K., 1994, which is incorporated by reference as if fully set forth herein.

Since the PMT's gain varies with temperature much less than that of the APD discussed previously, it is generally not necessary to compensate the device by changing the gain or determining the bias voltage. Instead, it is sufficient to use a simple multiplier derived from PMT characteristic curves, such as those shown in FIG. 3, which can be applied to the final PMT reading via the reporting software.

In order to calibrate the PMT, calibration microspheres with a known quantity of florescence are presented to the instrument, and flow through the system just as a normal sample would be acquired. While the calibration microspheres are being measured by the measurement system, the bias voltage is varied until a predetermined signal level is obtained.

This method is an iterative process where statistics of a set of microsphere readings are computed and used to terminate the process if the desired tolerance has been met. If the error is not small enough, then the results from the two previous iterations may be used to predict the next PMT bias setting. The equation of a line, y=m*x+b is employed in the process, where the slope m is defined by the previous bias and resultant fluorescent measurements. If the transfer function of the PMT's bias voltage to current gain was linear, the final solution could be attained directly and tested with one additional measurement. However, since the PMT's bias to current gain transfer function increases exponentially with increasing bias voltage, the linear method only works over a relatively small segment of the curve, thus requiring several iterations to meet final tolerance requirements.

Interestingly, when the PMT voltage versus gain is plotted on a log-log graph (see FIG. 4), the transfer function appears as a straight line. The data in FIG. 4 was taken from "Photomultiplier Tube—Principal to Application," Hamamatsu Photonics K.K., 1994.

Figure 4:
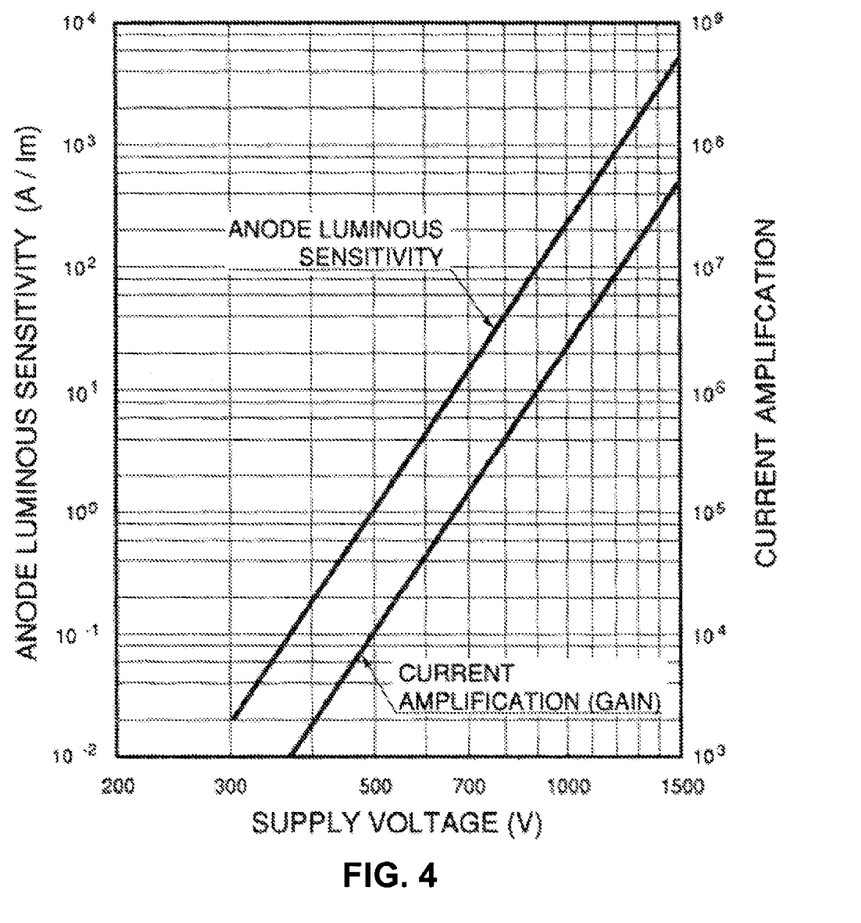
FIG. 4 is a graph illustrating one example of the log of gain of a PMT as a function of the log of the PMT bias voltage.

As stated earlier, the internal dynode count and the applied bias voltage govern the current amplification of a PMT. For a fixed level of light, as shown in Equation 1, the output current is proportional to V raised to the Nth power, where V is the applied bias voltage, N is the number of dynodes, and A is a constant of proportionality that encompasses several physical aspects of the PMT.

$$i = A * V^N \quad (1)$$

Taking the logarithm of each side of Equation 1 results in the following equation:

$$\log(i) = N * \log(V) + \log(A) \quad (2)$$

that can be rewritten as a simple and familiar first order linear equation:

$$y = m * x + b \quad (3)$$

where $y=\log(i)$, $m=N$, $x=\log(V)$, and $b=\log(A)$. Using this logarithmic transformation, it is now possible to perform a shortened calibration operation with as few as three sample measurements.

For example, in one embodiment, a method for controlling one or more parameters of a flow cytometer type measurement system includes setting a voltage of a PMT of the measurement system at a first value and a second value. The method also includes measuring an output current of the PMT at the first and second values. In addition, the method includes determining a calibration voltage of the PMT from a log of the first and second values versus a log of the output currents at the first and second values. The method further includes applying the calibration voltage to the PMT, and testing the PMT to determine if the one or more parameters of the PMT are within predetermined tolerances.

One specific example of such a method is outlined in steps 1 through 7 below.

1. Set the PMT voltage to a value proximate or at the low end of its range ($V=V_L$) and obtain a measurement ($i=i_L$).
2. Set the PMT voltage to a value proximate or at the high end of its range ($V=V_H$) and obtain a measurement ($i=i_H$).
3. Take the log of all four values.
4. Compute the slope m and intercept b.
5. Solve for the target PMT setting (in log space) $x_{cal}$.
6. Take the anti-log of $x_{cal}$ to obtain the PMT calibration voltage $V_{cal}$.
7. Apply $V_{cal}$, and test to determine if the desired tolerance has been met.

This method has been tested and has successfully converged each time well within tolerance. If the tolerance has not been met, an acceptable answer would likely result by generating a new slope and intercept in log space using the previous computed $V_{cal}$, $i_{cal}$ and $V_H$, $i_H$. The point $V_{cal}$, $i_{cal}$ is likely to be relatively close to the final PMT voltage, and only a short traversal along the new line may be required produce an acceptable answer. In this case, four sample measurements would be used to find the proper calibration voltage.

Another method for calibrating a detector of a flow cytometer type measurement system advantageously decreases the calibration iterations by using successive approximation. In one embodiment, a method for controlling one or more parameters of a flow cytometer type measurement system includes determining a calibration voltage of a detector of the measurement system using successive approximation, as shown in step 50 of FIG. 5. When all possible calibration voltages have been applied to the detector without achieving a successful calibration, the method may exit calibration with a failure, as shown in step 52. Since the detector may be an APD, a PMT, or any other detector suitable for the measurement system, each detector voltage may be compared against a detector voltage limit, as shown in step 54. If the calibration voltage exceeds the voltage limit, a different calibration voltage may be determined by repeating at least step 50.

Figure 5:
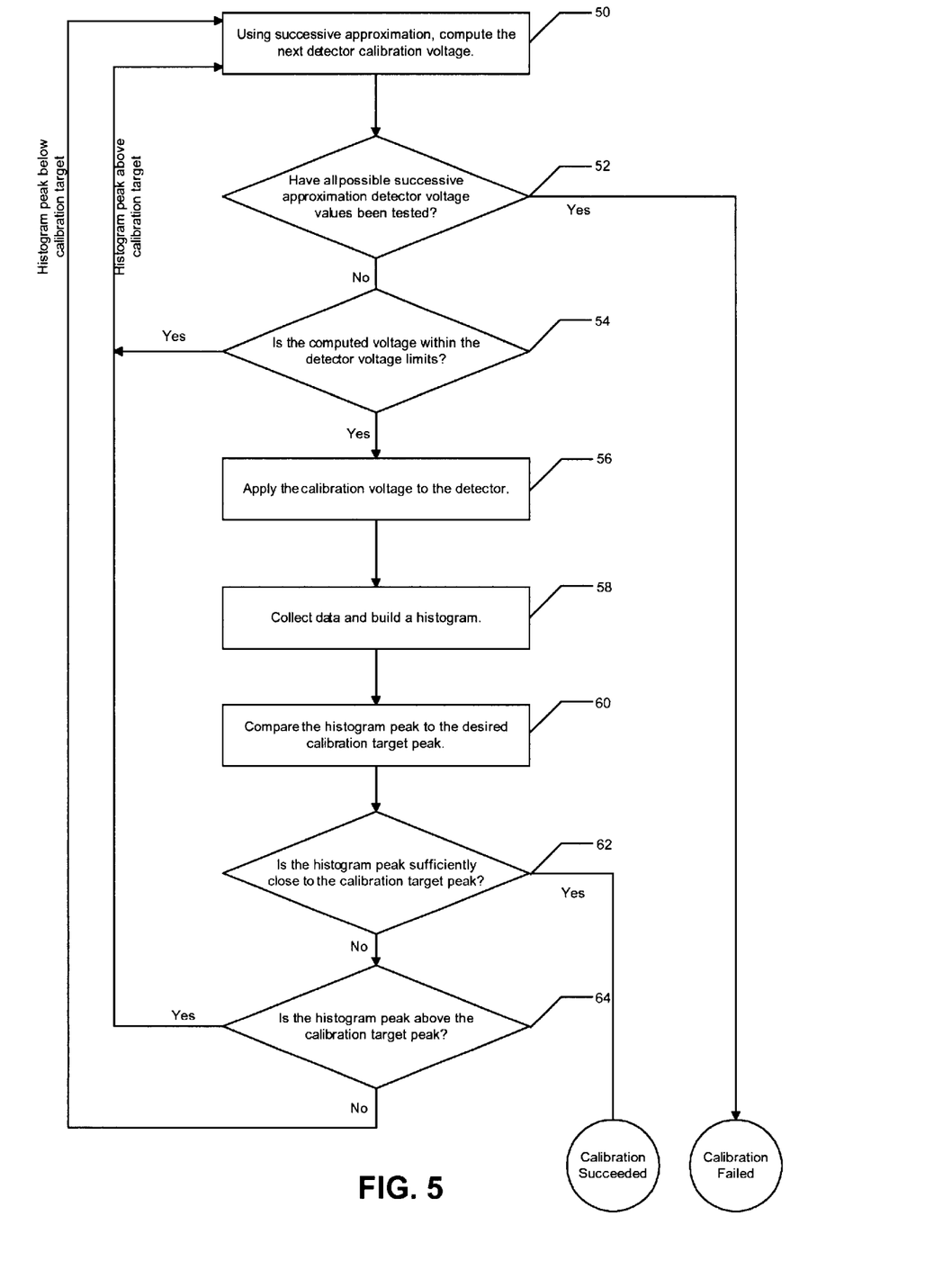
FIG. 5 is a flow chart illustrating one embodiment of a method for controlling one or more parameters of a flow cytometer type measurement system.

As shown in steps 56, 58, and 60, the method applies the calibration voltage to the detector, collects data from the detector, and may include building a histogram of the collected data, computing the peak value of the histogram, and comparing the histogram peak value to a calibration target peak value. If the histogram peak value is sufficiently close to the calibration target peak value, calibration may be ended, as shown in step 62.

The method may also include determining if the histogram peak value is above the calibration target peak value, as shown in step 64. The output of step 64 may be used to modify the next calibration voltage generated by the successive approximation method in step 50.

Although the method is described above with respect to histograms, it is to be understood that the method may be performed using any appropriate statistical measurements. For example, any suitable method of determining detector signal level may be used, which may, but need not, include statistical methods of determining the measurement from a collection of bead samples such as mean, median, etc.

In particular, successive approximation merely tries up to N times to make the measured value equal the target value by setting and clearing bits in a command word. In one embodiment, the method may include collecting and processing detector samples to determine the detector signal level. In one such embodiment, the method may include comparing the detector signal level to a calibration target signal level and if the detector signal level is above the calibration target signal level, then reducing the detector bias voltage and repeating the determination of the calibration voltage. In another such embodiment, the method may include comparing the detector signal level to a calibration target signal level and if the detector signal level is not within a predetermined range of the calibration target signal level, then repeating the determination of the calibration voltage until all desired detector voltage levels have been attempted.

One particular example of such a method may include the following steps.

1. Initialize a bit mask and a DacCmd value to $2^N$. For a 12 bit Dac ("Digital-to-Analog Converter"), N=12. In this example, the bit mask=4096, and the DacCmd value=4096. The Dac may include any suitable Dac such as those commercially available from Analog Devices, Inc., Norwood, Mass.

2. Use the current mask bit to clear the corresponding bit in DacCmd. We are either driving beyond the target or beyond the detector maximum voltage limit.
3. Shift the mask one bit to the right (e.g., to move to the next most significant bit).
4. If the mask is 0, then all possible bits have been tested and a sufficient calibration has not been achieved. The method may proceed to step 12.
5. Or mask into DacCmd to set the next most significant bit.
6. Determine the detector voltage corresponding to this DacCmd binary value. Compare the detector voltage to the detector breakdown or maximum voltage. If the voltage exceeds the detector breakdown voltage, go back to step 2.
7. Send the DacCmd value (e.g., the voltage) to the measurement system.
8. Wait for the voltage change to take effect.
9. Compare the new histogram peak value to the calibration target peak value for this channel. If the histogram peak is above the calibration target, go back to step 2.
10. If the histogram peak is not close enough to the desired target, go to step 3.
11. Calibration passed. Method complete.
12. Calibration failed. Method complete.

The example method described in steps 1-12 may include any other step(s) described herein.

Some flow cytometer measurement systems use a hydrostatic focusing technique to separate the beads for individual measurement as they pass through two detection windows. The detection windows have a fixed size and physical separation. For example, the distance between the illuminated spots of light sources in the measurement system defines the separation.

Variations in the velocity of the underlying fluid transport will vary the length of time that the bead is present in a detection window and the separation time to pass from one window to the next. The final reading is proportional to the length of time that the bead is present in each detection window. In addition, the system also uses the intra-window transit time to determine when the second detection window is active (i.e., when a bead is located in the second detection window for measurement). If the time-wise alignment of the sample measurement to the actual bead presence differs from the value obtained during calibration, or the duration (dwell) time in the illumination window differs, measurement accuracy will be degraded.

If the measurement system is configured to maintain a substantially constant pressure of the fluid during measurements of the sample microspheres, the effect of temperature is the greatest contributor to velocity variation through changes in the fluid's velocity. The definition of viscosity is the measure of a fluid's resistance to flow. The volume of fluid that flows per unit time through a tube of radius R and length L at pressure P can be expressed using Poiseuille's equation:

$$V/T = (\pi * R^4 * P)/(8 * N * L) \quad (4)$$

where V/T is volume per unit time (proportional to velocity), and N is viscosity in units of poise. The flow chamber's capillary, while having rectangular rather than round dimensions, can be treated as a simple tube. Thus, bead velocity is inversely proportional to the viscosity of the fluid transport as defined in Poiseuille's equation above.

The major component of the fluid used as a flow cytometer measurement system's bead transport is water. Over the 15° C. to 30° C. operating temperature range, the viscosity changes from 1.139 to 0.7975 centipoise, which is a significant 43% variation. The above viscosity values were obtained from the Handbook of Chemistry & Physics, 61st edition, "The Viscosity of Water 0 to 100° C." The velocities of the sheath and sample fluid also change by about 43% as does the velocity of the bead. Therefore, the operating temperature may be measured and may be used to determine the viscosity of the fluid. Accordingly, the velocity of the fluid may be determined from a table, from Poiseuille's equation, or from predetermined values of velocity versus temperature. In such embodiments, the method may include controlling a pressure of the fluid during measurements of sample microspheres based on the velocity.

In addition, the viscosity of the fluid may be used to determine the bead velocity. As such, the transit time can be extracted and corrected in real time. If the temperature of the fluid does not substantially change during sample measurements, monitoring the temperature and determining the velocity may be performed prior to performing measurements of the sample microspheres with the measurement system. However, the steps of the method may also be performed in real time.

Accordingly, one method for controlling one or more parameters of a flow cytometer type measurement system includes monitoring a temperature of a fluid that will flow through the flow cytometer type measurement system. Sample microspheres are disposed in the fluid. The method also includes determining a velocity of the sample microspheres in the measurement system from a viscosity of the fluid at the temperature. In some embodiments, the method may also include determining a length of time that one of the sample microspheres will be present in a detection window of the measurement system based on the velocity. In another embodiment, the method may include determining a length of time in which one of the sample microspheres will travel from one detection window of the measurement system to another detection window of the measurement system based on the velocity. In addition, the method may include determining when one of the sample microspheres will be present in a detection window of the measurement system based on the velocity. Furthermore, the method may include controlling a sampling interval for one or more detection windows of the measurement system to compensate for the velocity.

The intra-window transit time may be measured and saved to the system's non-volatile memory or to a computer that controls the system during the initial calibration procedure. The measured transit time may then be used during subsequent sample runs to properly time the sampling interval of the second detection window. The intra-window transit time can be shortened or lengthened to compensate for viscosity changes. The temperature at which the system was calibrated versus the current temperature can be used to determine the amount of correction to be applied. A simple table of temperature vs. viscosity factors could be stored either in the computer that controls the system or in the system's non-volatile memory. In either case, the transit time correction factor may be computed from the table and applied before a sample run commences. Alternatively, any other suitable method known in the art can be used to determine the correction factor.

The method may also include determining one or more properties of output signals of the measurement system from the velocity. For instance, the length of time that the bead is present in the detection windows determines the amplitude and shape of the detectors' output electrical pulses. The pulses then pass through an analog low pass filter, which has a significant effect on both amplitude and shape tending to reduce amplitude and stretch the pulse width. The post-filter pulse is digitized, and the area under the pulse is measured resulting in a value approximately proportional to the light level.

In addition, the method may include correcting the output signals for error due to the velocity using correction factors. The correction factors may be determined using empirical measurements. It stands to reason that a table of correction factors for pulse width changes due to flow rate variations may be constructed using empirical measurements. The table could be stored in either the system's memory or on a controlling computer coupled to the system.

Another method to compensate for velocity changes due to temperature variations is to change the applied fluid pressure in proportion to the viscosity change. This will result in the velocity remaining constant, therefore the time within each or between measurement windows will not change significantly. The method may be performed using Poiseuille's equation directly in real time or at the beginning of a sample run, or via a predetermined table computed from Poiseuille's equation, or via another method, in order to set the proper pressure dynamically.

These methods have proven to provide a great improvement over the constant pressure scheme, but additional compensation for temperature variations may be desirable. Thus, another method is described herein, which may be used separately from the above described method or in combination with the above described method to provide a fine-tuning mechanism. Unlike the method described above, this method employs an optical mechanism. In addition, the method may use a measurement and control algorithm. However, as described herein, despite the added optical mechanism and the algorithm, the method is relatively inexpensive and quick.

The distance between illumination spots (e.g., laser spots) is initially set when optical elements of a flow cytometer type measurement system are assembled. As the distance between the illumination spots (e.g., or light beams) decreases, the effect of velocity changes on bead transport time is minimized, since the bead has a shorter distance to travel between detection windows.

The minimum separation distance is further defined by the vertical illumination profile of each light beam (i.e., the profile of each beam in a direction substantially parallel to the direction in which microspheres flow through the measurement system). For example, if the beam intensities fall off rapidly from peak to shoulder, and there are no secondary maxima, it is possible to place the beams relatively close together, since light from one light source will not tend to spill over into the illumination spot of the other. Care should be taken to avoid overlapping light beams since such an overlap would necessitate a complex compensation scheme between the classification and reporter channels thereby resulting in a sensitivity loss.

As described previously, it is important to keep the bead transit time between illumination spots substantially constant, which, in turn, substantially fixes the velocity and the time which a microsphere spends in the respective illumination windows.

One method for maintaining a substantially constant bead transit time involves measuring the average time it takes for a bead to transit the two detection windows in real time and to control the applied pressure as necessary to keep the transit time constant. According to one embodiment, a method for controlling one or more parameters of a flow cytometer type measurement system includes measuring a time in which a microsphere travels from a first detection window of the flow cytometer type measurement system to a second detection window of the measurement system. In one embodiment, the time may be an average time. The microsphere may be a sample microsphere or a calibration microsphere. Measuring the time may include measuring light scattered by the microsphere in the first and second detection windows. In another embodiment, measuring the time may include measuring light scattered by the microsphere in the first and second detection windows with one detector. In one such embodiment, the light scattered by the microsphere in the first and second detection windows is directed to the one detector by one beamsplitter. The method also includes altering an applied pressure of the measurement system such that the time is substantially constant. The method may be performed in real time. The embodiments described above may include any other step(s) described herein.

Unfortunately, the current optical design of most flow cytometer type measurement systems makes it impossible to detect every bead that passes through a second detection window where typically just the reporter fluorescence is measured because the fluorescence emission, which is not known in advance, may not be constant from bead to bead, and could very well be zero for some beads. The obvious solution would be to add an additional optical detector to measure the second illumination source's light scattered by the bead, but this adds significant cost to the system as an additional electronics and digital processing chain must also be added to process the new signal.

The proposed solution is both simple and inexpensive since it involves using the same scattered light detector to measure scatter in both detection windows. Since the current optics layout prevents scattered light in the second (reporter) window from reaching the scatter detector, it is necessary to reposition the detector such that it receives all light emitted or reflected from the bead. If this is done, a distinct peak approximately proportional to the scatter from each light source will be separately discernable by the downstream electronics.

Figure 6:
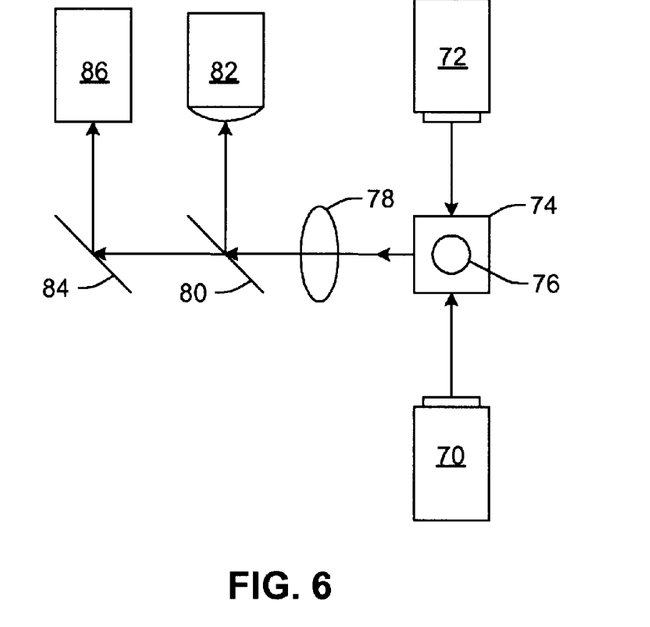
FIG. 6 is a schematic diagram illustrating a cross-sectional view of one embodiment of a portion of a measurement system that may be used to carry out at least one of the methods described herein.

FIG. 6 illustrates one embodiment of a measurement system that can be used to perform the methods described herein. As shown in FIG. 6, the measurement system includes light sources 70 and 72. Light source 70 may be, for example, a laser that emits light having a wavelength of about 639 nm. This laser may be suitable for providing illumination for a classification channel of the measurement system. Light source 72 may be, for example, a laser that emits light having a wavelength of about 532 nm. This laser may be suitable for providing illumination for a reporter channel of the measurement system. Note that the illumination zones of each laser are not coincident along the axis of bead flow (not shown). Other light sources may be used in place of the examples described above. For example, the light sources and the wavelengths of the light sources may vary depending on the samples to be measured.

As shown in FIG. 6, both light sources 70 and 72 illuminate cuvette 74. In particular, light sources 70 and 72 are configured to illuminate bead 76 as it flows through cuvette 74. As further shown in FIG. 6, light sources 70 and 72 may be configured to illuminate the bead at substantially opposite angles of illumination. However, it is to be understood that the light sources may illuminate the bead at any suitable angles of illumination.

Light scattered by the bead due to illumination by both light sources may be collected by lens 78. Lens 78 may include any suitable lens(es) known in the art. In addition, lens 78 may be replaced by a reflective collector or may not be included in the system. Although lens 78 is shown to collect light at a collection angle of about 90° (with respect to light sources 70 and 72), it is to be understood that the lens may be arranged at any suitable collection angle with respect to the light sources.

Light collected by lens 78 is directed to beamsplitter 80. Beamsplitter 80 may include any suitable optical component known in the art such as a glass plate or dichroic filter. Beamsplitter 80 is configured to direct a portion of the light collected by the lens to detector 82. Detector 82 may be configured to detect light scattered by the bead due to illumination by both (or multiple) light sources. In this manner, with respect to the examples of the light sources provided above, detector 82 may be configured to detect light scattered by the bead, which has a wavelength of about 532 nm and about 639 nm. The detector may include any suitable detector known in the art such as a CCD device.

Detector 82 will, therefore, detect two different scatter signals for a single bead. The scatter signals will be detected at different wavelengths, which will be determined based on the wavelengths of the light sources. Since each light source will illuminate the bead at a different time as the bead passes through the cuvette, the times at which the different scatter signals are detected can be used to measure the time in which a bead, or microsphere, travels from a first detection window of the measurement system to a second detection window of the measurement system.

In addition, beamsplitter 80 is configured to transmit the other portion of the light collected by the lens. The transmitted portion of the light may be directed by optical component 84 to classification portion 86 of the detection subsystem of the system. Optical component 84 may include, for example, a folding mirror, a dichroic beamsplitter, a partially transmissive mirror, or any other suitable component known in the art. Alternatively, optical component 84 may not be included in the system depending on, for example, the placement of the classification portion of the detection subsystem. The classification portion of the detection subsystem may include any suitable components known in the art. In some embodiments, the classification portion of the detection subsystem may be configured as described and shown in FIG. 1. Another portion of the light that is transmitted by beamsplitter 80 may be directed to a reporter channel (not shown) of the detection subsystem. While this system uses the first illumination zone for classification, and the second for the reporter signal, use in a device that employs this technique is not restricted to these measurements. The florescent or scattered light could be used for another purpose, such as measurement of fluorescent reporter or other dyes within a cell, bead, or other particle.

The fluorescent emissions, if any, that are directed to detector 82 by beamsplitter 80 will add to the scatter signal, but will be of no consequence, since their magnitudes are well below that of the scattered light. As described above, the implementation shown in FIG. 6 employs beamsplitter 80, which may be a wavelength dependent beamsplitter, to redirect scattered light into the repositioned detector and does not modify the spectra applied to classification detectors. Obviously, other embodiments are possible. For example, it is conceivable to arrange the detectors such that no additional parts would be included. The system shown in FIG. 6 may be further configured as described herein.

Another embodiment of a method for controlling one or more parameters of a flow cytometer type measurement system includes measuring an average time in which microspheres travel from a first detection window of the flow cytometer type measurement system to a second detection window of the measurement system. The microspheres may include sample microspheres, calibration microspheres, or a combination thereof. The method also includes comparing the average time to a reference time in which a reference microsphere traveled from the first detection window to the second detection window. The method may or may not include measuring the reference time. In addition, the method includes altering an applied pressure of the measurement system if a difference between the average time and the reference time is larger than a predetermined value. In some embodiments, the predetermined value may be selected to compensate for known time variation mechanisms of the measurement system. In one embodiment, altering the applied pressure includes increasing the applied pressure if the average time is larger than the reference time. In a different embodiment, altering the applied pressure may include decreasing the applied pressure if the average time is smaller than the reference time. This method may also be performed in real time.

Figure 7:
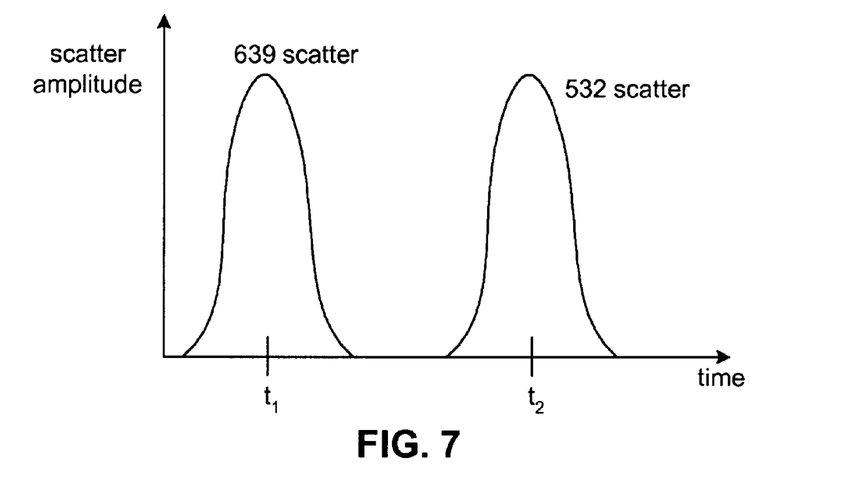
FIG. 7 is an illustration of the pulse train (i.e., scattered light measured at different times) that may be measured in one of the embodiments of the methods described herein.

The method described above provides a technique to directly control the system pressure such that the time between successive scatter pulses is substantially constant. This technique could be implemented using electronic hardware (e.g., counters, digital comparators, etc.) or software using the sampled signals measured by a digital signal processor or another suitable processor. In either embodiment, the methods are analogous, and the same results are obtained. A high level description of the algorithm is provided below in steps 1-6, and an example of a pulse train is illustrated in FIG. 7.

1. When the system is calibrated at a known pressure and temperature, the average transit time between successive scatter pulse peaks is measured and saved for later reference.
2. During a normal sample acquisition, the first scatter pulse from the red laser (or any other light source which first illuminates the bead) starts a timer. For example, as shown in FIG. 7, at $t_1$, a scatter pulse corresponding to illumination by a laser having a wavelength of 639 nm is detected. Accordingly, the timer is started at $t_1$.
3. When the second scatter pulse arrives, the timer is stopped. For example, when a scatter pulse corresponding to illumination by a laser having a wavelength of 532 nm is detected at $t_2$ as shown in FIG. 7, then the timer is stopped.
4. The value of the timer is then compared to the transit time that was measured during the calibration operation.
5. If the timer value is significantly larger than the calibration time, then one or more parameters of the pressure source (e.g., pump) are altered to increase its pressure. The parameter(s) of the pressure source may be altered by a processor. Alternatively, if the difference between $t_2$ and $t_1$ is larger than $t_{cal}$, then the pressure of the pressure source may be increased. $t_{cal}$ may be a predetermined value that defines acceptable variation in the transit time of the beads.
6. If the timer value is significantly smaller than the calibration time, then one or more parameters of the pressure source may be altered to reduce its pressure. The one or more parameters may be altered by a processor. Alternatively, if the difference between $t_2$ and $t_1$ is smaller than $t_{cal}$, then the pressure of the pressure source may be decreased. $t_{cal}$ used in steps 5 and 6 may have the same value.

To keep this "control system" relatively stable, there are several things that can be taken into consideration. For instance, the method may be performed such that the system is not controlled to try and make positive or negative pressure corrections for every bead event that passes through the system. Some averaging method may be employed to compensate for a known time variation mechanism called "bead jitter" which is believed to result, at least in part, from a velocity gradient in the sample core. Also, the threshold of the time error that causes a pressure correction should be carefully chosen. The magnitude of the error may be best used as input to the controller that determines the amount of pressure correction. It is quite possible that a classic integral-differential controller can be used for well behaved operation.

While the correction factors listed above can be used to correct a major portion of the measurement error prior to measurements of sample microspheres, a fine correction may also be made during a measurement process that will compensate for residual errors that may be present after the above techniques are implemented. For example, one method for controlling one or more parameters of a flow cytometer type measurement system includes monitoring the one or more parameters of the measurement system during measurements of sample microspheres by the measurement system. The method also includes altering the one or more parameters in real time based on the monitored parameter(s). For example, as described above, the one or more parameters that are monitored and altered may include a parameter of a PMT of the measurement system. In addition, error sources other than those identified in this description may also be eliminated using this procedure.

A flow cytometer type measurement system identifies microspheres that pass through the system based on the measured intensity of two or more dyes internal to the microspheres. This identification technique can also be used to identify a calibration microsphere that contains known quantities of fluorescent intensity in all channels (both reporter and classification). After the calibration microsphere measurement is known, a fine correction factor can be applied to the reporter and/or classification channels for sample microsphere measurements.

A complication of this technique may arise when distinguishing the calibration microspheres from sample microspheres. For example, a new spectral address for the calibration microspheres could be created based on the dye level combinations, but this would reduce the multiplexing capabilities of the system by N−1. Another technique is to identify the calibration microspheres by making their diameters larger or smaller than those of the sample microspheres.

The measurement system may measure light scattered by the microspheres at 90° to the illumination plane. The level of the scattered light is used to identify multiple microspheres that may be stuck together in a group or may be passing substantially simultaneously through the illumination zone. For example, the scattered light is generally proportional to the volume of all particles that exist in the illumination zone; thus, multiple microspheres will have greater scatter signals than single microspheres. Since the majority of the microspheres will usually pass through the illumination zone as single objects, by looking at the population events, it is easy to identify those events that do not belong to single beads. Generally, two and sometimes three microspheres aggregate and produce a scatter signal that is higher than that produced by single microspheres. The scatter signal level for single microspheres is typically measured during assay development as the assay format can have an effect on the scatter signal.

Using calibration microspheres having a diameter that is smaller, rather than larger, than a diameter of the sample microspheres is desirable since it will be easier to identify the calibration microspheres from any multiple microsphere combinations that may pass through the illumination zone. Accordingly, monitoring the parameter(s) of the measurement device may be performed using measurements of calibration microspheres, which have diameters that are less than diameters of the sample microspheres. In addition, the one or more parameters that are monitored and altered may include output signals produced by detectors of the measurement system, which are responsive to light scattered by the sample microspheres. For example, if the ratio of calibration microsphere diameter to sample microsphere diameter is known, it is also possible to use the calibration microspheres to fine-tune the scatter measurement level as well.

At least some of the calibration microspheres may also have different spectral addresses. In this manner, a series of different calibration microspheres may be used to enhance the above calibration method. For example, by using diameter as the first discriminator, the spectral address of the calibration microspheres may be the secondary discriminator in the calibration space just as it is in the sample space. Having multiple calibration levels, which are separated sufficiently in the classification space to discriminate the microsphere's identities, could be used in the following implementations.

For example, the one or more parameters that may be monitored and altered may include linearity in the measurements of the sample microspheres. The measurements during which parameter(s) of the measurement device are monitored and altered may include measurements of a classification channel of the measurement system. Altering the parameter(s) of the measurement device, in this embodiment, preferably corrects any non-linearity in the measurements. In this manner, the multiple calibration levels may be used to detect and correct non-linearity in the classification space. The current measurement system uses a single point calibration, and as such errors due to system non-linearity cannot be corrected. In a two-dye bead system, expressed in two dimensions, this non-linearity could be thought of as a morphing of the classification space in a plane based on the observed locations of the classification microspheres. Correcting the non-linearity improves the classification accuracy of microspheres in that plane. This technique can be extended to any number of dimensions with similar effects.

The multiple calibration levels may also be used to detect and correct non-linearity on the reporter signal. Similar to the technique described above, the reporter channel may also undergo a single calibration point in current measurement systems. Detecting and correcting non-linearity in the reporter channel may be performed as described above. For example, the measurements during which parameter(s) of the measurement system are monitored and altered may include measurements of a reporter channel of the measurement system. Furthermore, the measurements during which parameter(s) of the measurement system are monitored and altered may include measurements of a reporter channel and a classification channel of the measurement system. In this manner, non-linearity in the classification and reporter channels can be monitored and corrected substantially simultaneously.

In another example, the one or more parameters of the measurement system that may be monitored and altered include a dynamic range of the measurement system. For example, the multiple calibration levels may also be used for real time determination of the system's dynamic range. The measurement system has a finite linear range. By utilizing a different reporter calibration level on one or more uniquely identified calibration microspheres, it is possible to identify the lower limit of detection and/or the upper limit of detection where the system becomes nonlinear due to signal clipping.

In some embodiments, the multiple calibration levels may be used for determination of classification system health. In this manner, the one or more parameters that are monitored and altered may include measurement system health. The measurement system health may include health of a classification channel, health of a reporter channel, or a combination thereof. For example, if the collection of individual solutions described above fails to compensate the system for temperature or other effects, the calibration microsphere fluorescence classification levels will tend to be farther from their expected values. A threshold level could be set, and the calibration microsphere fluorescence classification levels may be compared to the threshold level. If the calibration microsphere fluorescence classification levels fall on a selected side of the threshold level, a warning may be presented to the system operator or may be sent to a computer coupled to the measurement system that the results are questionable. The warning may be a visual output signal and/or an audible output signal. In a similar manner, the multiple calibration levels may be used for determination of the reporter system health. Similar to determination of classification system health, uncorrectable errors in the reporter system could be identified and reported to the system operator or a computer coupled to the measurement system.

Furthermore, the multiple calibration levels may be used to extend the linear dynamic range of the reporter channel. In this manner, altering the parameter(s) of the measurement system may include extending a linear dynamic range of a reporter channel of the measurement system. By including several levels of bright calibration microspheres that exist in the nonlinear region, it is possible to map actual measured fluorescent levels to their linear equivalents. A smooth mapping from measured to expected curve could be constructed from the calibration data by interpolating between individual calibration microsphere values. Thus, the linear, useful measurement range of the system may be significantly extended if the sample microspheres in the nonlinear region are adjusted using the curve.

In the above description, several measurement error contributors and real time correction techniques for each have been identified. In addition, a real time fine-tuning method using small diameter calibration microspheres that could be included in microsphere sample mixes has been created. Added features of the fine-tuning process include real time identification of system health, correction of non-linearities in one or more channels, as well as the significant extension of the measurement system's useful reporter dynamic range.

Program instructions implementing methods such as those described herein may be transmitted over or stored on the carrier medium. The carrier medium may be a transmission medium such as a wire, cable, or wireless transmission link, or a signal traveling along such a wire, cable, or link. The carrier medium may also be a storage medium such as a read-only memory, a random access memory, a magnetic or optical disk, or a magnetic tape.

In an embodiment, a processor may be configured to execute the program instructions to perform a computer-implemented method according to the above embodiments. The processor may take various forms, including a dedicated processing board employing digital signal processing chips or field programmable gate arrays, a personal computer system, mainframe computer system, workstation, network appliance, Internet appliance, personal digital assistant ("PDA"), television system or other device. In general, the term "computer system" may be broadly defined to encompass any device having one or more digital signal processing elements or other processing elements.

The program instructions may be implemented in any of various ways, including procedure-based techniques, component-based techniques, and/or object-oriented techniques, among others. For example, the program instructions may be implemented using ActiveX controls, C++ objects, JavaBeans, Microsoft Foundation Classes ("MFC"), or other technologies or methodologies, as desired. In the case of a FPGA implementation, the use of high level languages such as VHDL may be employed to design the signal processing circuit embedded within the device.

It will be appreciated to those skilled in the art having the benefit of this disclosure that this invention is believed to provide methods for controlling one or more parameters of a flow cytometer type measurement system. Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A method for controlling one or more parameters of a flow cytometer type measurement system, comprising:
    monitoring a temperature proximate to the flow cytometer type measurement system; and
    altering an output signal of a photomultiplier tube of the measurement system in response to the temperature using a characteristic curve for the photomultiplier tube to substantially correct for variation in a gain of the output signal of the photomultiplier tube due to the temperature.

2. The method of claim 1, wherein the gain of the photomultiplier tube varies approximately linearly in response to the temperature.

3. The method of claim 1, wherein the photomultiplier tube is part of a reporter channel of the measurement system.

4. The method of claim 1, wherein the characteristic curve for the photomultiplier tube varies with detection wavelength and cathode construction of the photomultiplier tube.

5. A method for controlling one or more parameters of a flow cytometer type measurement system, comprising:
    setting a voltage of a photomultiplier tube of the measurement system at a first value and a second value;
    measuring an output current of the photomultiplier tube at the first and second values;
    determining a calibration voltage of the photomultiplier tube from a log of the first and second values versus a log of the output currents at the first and second values;
    applying the calibration voltage to the photomultiplier tube; and
    testing the photomultiplier tube to determine if one or more parameters of the photomultiplier tube are within predetermined tolerances, wherein if the one or more parameters are determined to be outside of the predetermined tolerances, the method further comprises:
        using the calibration voltage to determine a new calibration voltage; and
        repeating the steps of determining, applying, testing, and using until the one or more parameters are determined to be within the predetermined tolerances.

6. The method of claim 5, wherein the first value comprises a voltage value proximate to a low end of the photomultiplier input voltage range.

7. The method of claim 5, wherein the second value comprises a voltage value proximate to a high end of the photomultiplier input voltage range.

* * * * *

UNITED STATES PATENT AND TRADEMARK OFFICE
Certificate

Patent No. 7,523,637 B1                                                     Patented: April 28, 2009

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Wayne D. Roth, Leander, TX (US).

Signed and Sealed this Fifth Day of October 2010.

<div align="right">

HEZRON E. WILLIAMS
*Supervisory Patent Examiner*
Art Unit 2856
Technology Center 2800

</div>